United States Patent
Feldstein et al.

(10) Patent No.: US 7,278,843 B2
(45) Date of Patent: Oct. 9, 2007

(54) METHODS FOR FINE POWDER FORMATION

(75) Inventors: Robert Feldstein, Yonkers, NY (US); Solomon S. Steiner, Mount Kisco, NY (US)

(73) Assignee: MannKind Corporation, Valencia, CA (US)

(*) Notice: Subject to any disclaimer, the term of this patent is extended or adjusted under 35 U.S.C. 154(b) by 646 days.

(21) Appl. No.: 10/224,676

(22) Filed: Aug. 20, 2002

(65) Prior Publication Data

US 2002/0193290 A1    Dec. 19, 2002

Related U.S. Application Data

(62) Division of application No. 09/543,309, filed on Apr. 5, 2000, now Pat. No. 6,440,463.

(60) Provisional application No. 60/127,699, filed on Apr. 5, 1999.

(51) Int. Cl.
*B29B 9/00* (2006.01)

(52) U.S. Cl. .................. 425/6; 425/7; 264/13; 424/489

(58) Field of Classification Search ................ 424/489; 425/5, 6, 7; 264/13
See application file for complete search history.

(56) References Cited

U.S. PATENT DOCUMENTS

| | | | |
|---|---|---|---|
| 3,673,698 A * | 7/1972 | Guerard ........................ 34/284 |
| 3,873,651 A * | 3/1975 | Mosley et al. ................ 264/0.5 |
| 4,981,625 A * | 1/1991 | Rhim et al. .................... 264/13 |
| 5,017,383 A | 5/1991 | Ozawa et al. |
| 5,019,400 A | 5/1991 | Gombotz et al. |
| 5,196,049 A * | 3/1993 | Coombs et al. ................ 75/338 |
| 5,208,998 A | 5/1993 | Oyler, Jr. |
| 5,775,320 A | 7/1998 | Patton et al. |
| 5,817,343 A | 10/1998 | Burke |
| 5,922,253 A * | 7/1999 | Herbert et al. .................. 264/5 |
| 5,997,848 A | 12/1999 | Patton et al. |
| 6,045,828 A | 4/2000 | Bystrom et al. |
| 6,051,256 A | 4/2000 | Platz et al. |
| 7,125,566 B2 | 10/2006 | Etter |

FOREIGN PATENT DOCUMENTS

| | | |
|---|---|---|
| WO | WO90/13285 A1 | 11/1990 |
| WO | WO94/25005 A1 | 11/1994 |
| WO | WO96/36317 A1 | 11/1996 |
| WO | WO97/35562 A1 | 10/1997 |

OTHER PUBLICATIONS

Young, et al., "Encapsulation of lysozyme in a biodegradable polymer by preparation with a vapor-over-liquid antisolvent," *Journal of Pharmaceutical Sciences* 88:640-650 (1999).

* cited by examiner

*Primary Examiner*—Robert Davis
*Assistant Examiner*—Maria Veronica Ewald
(74) *Attorney, Agent, or Firm*—Pabst Patent Group LLP

(57) ABSTRACT

Improved methods for forming fine particles of a material have been developed, wherein the method steps include dissolving the material in a solvent to form a dilute solution, immobilizing the dilution solution, and then removing the solvent to yield particles of the material. Methods of immobilizing the dilute solution include freezing, gelation, and chelation. In a preferred embodiment, the immobilized solvent is removed by lyophilization, i.e. reducing the ambient pressure while avoiding application of sufficient heat to power a phase transition. Essentially any material and solvent for the material can be used in the methods described herein. Proteins and peptides in an aqueous solvent are the preferred systems.

3 Claims, No Drawings

METHODS FOR FINE POWDER FORMATION

CROSS-REFERENCE TO RELATED APPLICATIONS

This application is a divisional of U.S. Ser. No. 09/543,309, files Apr. 5, 2000 now U.S. Pat. No. 6,440,463, which claims the benefit of U.S. provisional Application No. 60/127,699, filed Apr. 5, 1999.

BACKGROUND OF THE INVENTION

This invention generally relates to methods for making fine particles, especially particles formed of proteins and peptides.

Fine uniform particles, or powders, are useful in a variety of applications, including medical and pharmaceutical applications such as drug delivery and diagnostics. One example is in aerosol delivery systems to deliver drugs to the lung. The size of the particles delivered directly affects whether the drugs are delivered to the lungs as desired. Accordingly, processing methods which result in fine powders of uniform particles are highly desirable for pulmonary drug delivery, as well as other applications.

Current material processing techniques for making fine, uniform particles in these size ranges include micromilling and precipitation from a solvent. Micromilling, however, can produce locally extreme conditions (e.g., high temperatures) which are capable of altering proteins and peptides. These alterations are unacceptable for fragile materials, especially those intended for administration in pharmaceutical applications. Therefore, precipitation from solvents has been widely used to produce fine powders from fragile materials. Examples of precipitation from solvent methods include anti-solvent systems and super saturation produced by externally changed solubility.

The effectiveness of conventional precipitation from solvent methods, however, generally is limited by the mobility of the precipitate, which allows for assembly of amorphous "clusters" of variable size or microcrystalline particles. The mass of the resultant particle is controlled primarily by the mobility of the precipitant during the interval between supersaturation and exhaustion due to deposition on growing nucleation sites. For example, if the precipitant has a low mobility, the particles formed will have a low mass, while greater mobility generally increases the mass of the resulting particle. Simply diluting the solution is insufficient, since dilute solutions generally do not result in a precipitate. Therefore, in order to obtain fine particles using precipitation from solvent methods, it would be desirable to be able to control, i.e. restrict, the mobility of the precipitant while solvent removal is undertaken.

It is therefore an object of this invention to provide methods of forming fine, uniform particles from fragile materials.

It is another object of this invention to provide methods of forming fine particles using solvent removal methods having reduced precipitant mobility.

SUMMARY OF THE INVENTION

Improved methods for forming fine particles of a material have been developed, wherein the method steps include dissolving the material in a solvent to form a dilute solution, immobilizing the dilution solution, and then removing the solvent to yield particles of the material. Methods of immobilizing the dilute solution include freezing, gelation, and chelation. In a preferred embodiment, the immobilized solvent is removed by lyophilization, i.e. reducing the ambient pressure while avoiding application of sufficient heat to power a phase transition. Essentially any cargo material and solvent for the material can be used in the methods described herein. Proteins and peptides in an aqueous solvent are the preferred systems.

DETAILED DESCRIPTION OF THE INVENTION

Fine powders are formed by immobilizing dilute solutions of the material forming the powder (i.e., the "cargo") and then removing the solvent.

As used herein, "powders" are particles having a diameter of less than about 500 µm. In a preferred embodiment, the particles have a diameter between about 0.5 µm and about 10 µm, which is generally required for effective pulmonary administration. The terms "powder" and "particles" are herein used interchangeably unless otherwise indicated.

The formation of droplets of a dilute solution of a cargo in a solvent and the subsequent removal of the solvent leave small residual product particles. If the droplet is frozen prior to removal, then the restricted mobility of the cargo may, despite rising local concentration, leave multiple smaller "product" particles per droplet and therefore provides a preferable processing technique.

Cargo

The cargo can be selected from any number of molecular species, or noninteractive combinations thereof. In a preferred embodiment, the cargo is a therapeutic or diagnostic agent. Examples of types of suitable molecular species include synthetic inorganic and organic compounds, proteins and peptides, polysaccharides and other sugars, lipids, and nucleic acid sequences and fragments of nucleic acids having therapeutic, prophylactic, or diagnostic activities.

Representative molecular species include vasoactive agents, neuroactive agents, hormones, anticoagulants, immunomodulating agents, cytotoxic agents, antibiotics, antivirals, antisense, antigens, and antibodies. Specific cargo examples include insulin, heparin, calcitonin, felbamate, parathyroid hormone and fragments thereof, growth hormone, erythropoietin, AZT (azidothymidine), ddI (didanosine), G-CSF (granulocyte colony-stimulating factor), GM-CSF (granulocyte-macrophage colony-stimulating factor), lamotrigine, chorionic gonadotropin releasing factor, luteinizing releasing hormone, β-galactosidase, argatroban, azelastine, taurolidine, and glucagon.

Proteins and peptides are the preferred cargo. As used herein, a "protein" consists of 100 amino acid residues or more, and a "peptide" has less than 100 amino acid residues. Representative examples include insulin and other hormones. Polysaccharides, such as heparin, also can be the cargo.

The cargo can be administered as an antigen, where the molecule is intended to elicit a protective immune response, especially against an agent that preferentially infects the lungs, such as mycoplasma, bacteria causing pneumonia, and respiratory synticial virus. In these cases, it may also be useful to administer the drug in combination with an adjuvant, to increase the immune response to the antigen.

The cargo also can be or include any genes that would be useful in replacing or supplementing a desired function, or achieving a desired effect such as the inhibition of tumor growth. As used herein, a "gene" is an isolated nucleic acid molecule of greater than thirty nucleotides, preferably one hundred nucleotides or more, in length. Examples of genes which replace or supplement function include the genes encoding missing enzymes such as adenosine deaminase (ADA), which has been used in clinical trials to treat ADA deficiency, and cofactors such as insulin and coagulation factor VIII. Genes which effect regulation can also be administered, alone or in combination with a gene supplementing or replacing a specific function. For example, a gene encoding a protein which suppresses expression of a particular protein-encoding gene, or vice versa, which induces expresses of a protein-encoding gene, can be administered as the cargo. Examples of genes which are useful in stimulation of the immune response include viral antigens and tumor antigens, as well as cytokines (e.g., tumor necrosis factor) and inducers of cytokines (e.g., endotoxin), and various pharmacological agents.

Cargo Solvent

The cargo can be dissolved in essentially any solvent or combination of solvents that is compatible with the cargo, as long as the vapor pressure of the solid phase of the solvent is greater than the vapor pressure of the cargo, at the processing pressures and temperatures selected. In a preferred embodiment, the solvent is water or a substantially aqueous solution, preferably greater than 90% water by weight. It is desirable that the solvent be nontoxic, at least in any residual quantities following solvent removal, particularly when the solvent is used to process cargo intended for pharmaceutical and medical applications.

Powder Formation Methods

The fine particles are made by (a) dissolved a material in a solvent to form a dilute solution; (b) immobilizing the dilution solution; and (c) removing the solvent from the immobilized solution, thereby yielding fine particles of the material. The immobilization method preferably is selected from freezing, gelation, and chelation. Removal of the solid phase solvent preferably is achieved by reducing the ambient pressure and not supplying sufficient heat to power a phase transition, i.e. lyophilization.

(i) Freezing in Liquid Nonsolvent

In a preferred method, a dilute aqueous solution of cargo, such as a peptide, is sprayed as a mist of fine droplets from a nebullizer, sonicator, or other atomization device. The mist is permitted to fall into a liquid which is (1) a nonsolvent for the material and (2) at a temperature low enough to freeze the dilute solution, thereby forming tiny "ice" pellets (i.e. frozen solution) containing a cargo content, the concentration of which correlates to the initial concentration of the dilute aqueous solution. Next, the liquid (e.g., nitrogen) is vaporized, and the solvent (e.g., water) is sublimed at low pressure to yield fine particles of the cargo (e.g., peptide). In an alternative embodiment, a dilute solution of the material can be atomized directly into a liquid which is (1) a nonsolvent for the material and (2) at a temperature low enough to freeze the dilute solution. Preferably, the liquid is selected from nitrogen, argon, oxygen, helium, and carbon dioxide.

In a variation of the process described above, a liquid droplet falling into a bath of liquid passes through a region of decreasing temperature. Within this transition region, the dew point declines, since it cannot exceed the ambient temperature. Consequently, when using an aqueous solvent, the partial pressure of water vapor on the surface of the droplet will decrease, causing surface evaporation. Evaporation removes 540 cal. of heat per gram of water, reducing the temperature of the droplet. Once the droplet reaches 0° C., heat loss of an additional 80 cal. of heat per gram of water will cause the droplet to freeze into an "ice spherical." This freezing process occurs rapidly, due to the small size of the droplet, despite the moderate thermal conductivity of ice. The temperature of the ice spherical continues to decrease in the liquid nitrogen environment, with a corresponding decrease in dew point and water vapor partial pressure. The surface of the ice spherical sublimes, removing 620 cal. of heat per gram of water, thereby lowering the temperature of the shrinking core and increasing the concentration of cargo molecules on the evaporating surface. The surface mobility of these molecules controls the particle size of the final product. For example, the lower the mobility, the less growth can occur and the smaller the resulting particle. The sublimation process also may have a dynamic component that interferes with surface mobility, that is, the rapid surface ablation may produce jets at the surface which could interfere the motion of particles. As the ice spherical shrinks, a more concentrated cargo shell evolves. Competition between nucleation sites determines the final product particle form and the size distribution. Greater dilution of the original solution therefore generally yields smaller particles.

(ii) Freezing in Vacuum and/or Dry Gas

In another embodiment, the initial dilution solution is sprayed directly into a vacuum or low pressure chamber. The pressure must be above the vapor pressure of the cargo over the entire freeze/sublime profile (to prevent cargo from being evaporated) and must be below the triple point pressure of the solvent (to prevent liquid state mobility from aiding cargo segregation). The emerging droplet will surface boil—e.g., removing approximately 20% of the mass in water. The droplet then will cool, freeze, and sublime, as the temperature approaches a terminal temperature at the dew point at the external vapor pressure (i.e. partial pressure). Despite the relatively low ablation rate, part of the lyophilizing cycle is provided by spherical formation.

In another embodiment, the initial dilute solution is sprayed directly into an ultra-dry gas, preferably argon. By keeping the dew point sufficiently low by solvent removal (external to the processing chamber), then the boiling, freezing, and sublimation will proceed as in vacuum. The argon beneficially provides additional aerodynamic drag, which limits the speed at which the droplet/spherical falls from the atomizer through the chamber. Optional external infrared heaters can be used with transparent spray chamber walls to transmit the energy required to power solvent sublimation without melting the solvent. Thus, lyophilization can be combined with formation.

(iii) Reactor with Controlled Counter Current Gas Stream

In a variation of the ultra-dry argon system described above, a cold nitrogen reactor is used instead. For example, the nitrogen reactor is in the form of a tall column having liquid nitrogen at the bottom, a liquid nitrogen filling port near the bottom, and a vent and atomizer near the top. Cold, high-density, nitrogen settles over the liquid nitrogen surface. Then heat is added at a controlled rate to the nitrogen to evaporate a portion of the nitrogen, without increasing the temperature, since the liquid nitrogen is near its boiling point near atmospheric pressure. Evaporated nitrogen is permitted to "weep" (i.e. vent) out of the column at a rate to maintain the pressure of the column. In this method, the rate of heat addition is a critical operating parameter. For example, too much heat will actually lower the temperature by increasing the flow rate of cold nitrogen up the column. A droplet of dilute cargo solution atomized into the reactor will proceed through the surface evaporation, freezing, sublimation, and cooling cycle described above. The droplet/spherical will fall from the atomizer through the column with terminal velocity depending on its weight-to-drag ratio. If external infrared heaters are used to speed surface ablation, then the droplet/spherical size will further decrease as it falls through the column, and the terminal velocity consequently also will decrease. In other words, the droplet/spherical will decelerate during its descent due to evaporation. Accordingly, the nitrogen flow velocity up the column must be less than the aerodynamic terminal velocity of the smallest desired product particle to avoid being swept out of the column with the rising nitrogen stream. One way to control this process is to use a laser backscatter monitor, which can be used to control the particle fall rate by controlling liquid nitrogen heating rate.

Liquid nitrogen can be added continuously or intermittently during the evaporation process to maintain a relatively constant column profile. Product can be collected from the bottom of the column following evaporation of nitrogen remaining after solution atomization ceases.

(iv) Gelation and Chelation

The fine powders can be formed similarly to the methods described using gelation or chelation, rather than freezing as the immobilization technique, using standard gelling or chelating agents.

Fine Powder Applications

The fine powders made as described herein are useful in a variety of applications, particularly in pharmaceutical and medical applications, requiring uniform small particle size of fragile materials such as proteins and peptides. In one embodiment, the fine powder is included in an aerosol delivery system to deliver drugs or diagnostic agents to the respiratory system, particularly to the lungs. Aerosol delivery systems are described, for example, in U.S. Pat. Nos. 5,775,320 and 5,997,848 to Patton.

In another embodiment, the fine powder is included in an oral delivery system, for example, wherein the fine powder is formed into a tablet or encapsulated in a gelatin or starch capsule using standard techniques known in the art. The fine powders of prophylactic, diagnostic, or therapeutic agents also can be incorporated into formulations for administration by other routes.

Modifications and variations of the present invention will be obvious to those of skill in the art from the foregoing detailed description. Such modifications and variations are intended to come within the scope of the following claims.

We claim:

1. An apparatus for the formation of fine powders comprising an atomizer for atomizing a solution of a material dissolved in a solvent; a vessel comprising a means for immobilizing the solution following atomization and a means for removing the solvent from the immobilized solution by reducing the ambient pressure to a pressure sufficiently low to induce a phase transition in the solvent.

2. The apparatus of claim 1 wherein the means for immobilizing the solution comprises a fluid which is a nonsolvent for the material and is at a temperature low enough to freeze the dilute solution.

3. The apparatus of claim 2 wherein the vessel comprises a colunm having a vent near a top end of the colunm and the fluid is in liquid form near a bottom end of the column, wherein the apparatus further comprises a means for controlling the rate of heat added to the liquid.

* * * * *